United States Patent [19]
Bryant et al.

[11] Patent Number: 6,017,914
[45] Date of Patent: Jan. 25, 2000

[54] BENZO[B]THIOPHENE COMPOUNDS, INTERMEDIATES, FORMULATIONS, AND METHODS

[75] Inventors: Henry Uhlman Bryant; Michael John Martin; Ken Matsumoto, all of Indianapolis, Ind.

[73] Assignee: Eli Lilly and Company, Indianapolis, Ind.

[21] Appl. No.: 08/923,072

[22] Filed: Sep. 3, 1997

Related U.S. Application Data

[60] Provisional application No. 60/027,692, Oct. 10, 1996.

[51] Int. Cl.[7] ...................... C07D 333/54; C07D 333/56; C07D 409/00; A61K 31/38
[52] U.S. Cl. .................. 514/231.5; 514/324; 514/428; 514/471; 514/443; 544/146; 546/202; 548/565; 549/49; 549/58
[58] Field of Search .................. 514/324, 231.5, 514/428, 471, 443; 546/196, 527, 202; 544/146; 548/565; 549/49, 58

[56] References Cited

U.S. PATENT DOCUMENTS

| | | |
|---|---|---|
| 3,394,125 | 7/1968 | Crenshaw . |
| 3,413,305 | 11/1968 | Crenshaw . |
| 4,133,814 | 1/1979 | Jones et al. . |
| 4,230,862 | 10/1980 | Suarez et al. ............................ 546/237 |
| 4,358,593 | 11/1982 | Jones et al. ............................ 546/202 |
| 4,380,635 | 4/1983 | Peters ...................................... 546/202 |
| 4,418,068 | 11/1983 | Jones et al. ............................ 546/237 |
| 5,075,321 | 12/1991 | Schreiber ................................ 514/317 |
| 5,395,842 | 3/1995 | Labrie ..................................... 514/320 |
| 5,470,854 | 11/1995 | Angerer et al. ......................... 514/233 |
| 5,472,962 | 12/1995 | Koizumi et al. . |
| 5,484,798 | 1/1996 | Bryant et al. . |

FOREIGN PATENT DOCUMENTS

| | | |
|---|---|---|
| 062 503 | 10/1982 | European Pat. Off. . |
| 0 641 791 | 11/1992 | European Pat. Off. . |
| 0 617 030 | 3/1994 | European Pat. Off. . |
| 0 675 121 | 3/1995 | European Pat. Off. . |
| 0 699 673 | 8/1995 | European Pat. Off. . |
| WO 89/0289 | 4/1989 | WIPO . |
| WO 95 10513 | 4/1995 | WIPO . |
| WO 97/25033 | 10/1996 | WIPO . |

OTHER PUBLICATIONS

Crenshaw, R. R., et al., *J. Med. Chem.*, 14(12), 1185–1190 (1971).
Jones, C. D., et al., *J. Med. Chem.*, 27, 1057–1066 (1984).
Jones, C. D., et al., *J. Med. Chem.*, 35, 931–938 (1992).
Grese, et al., "Structure–Activity Relationships of Selective Estrogen Receptor Modulators: Modifications to the 2–Aryl-benzothiophene Core of Raloxifene," *J. Med. Chem*, 97, vol. 40 (2), 146–167 (1996).
Martin, et al., "Versatile Raloxifene Triflates," *Bioorg. Med. Chem. Lett.*, vol. 7, No. 7, 887–892 (1997).

*Primary Examiner*—Jeffrey Mullis
*Attorney, Agent, or Firm*—Gilbert T. Voy

[57] ABSTRACT

This invention relates to the field of pharmaceutical and organic chemistry and provides benzothiophene compounds, intermediates, formulations, and methods.

25 Claims, No Drawings

BENZO[B]THIOPHENE COMPOUNDS, INTERMEDIATES, FORMULATIONS, AND METHODS

This application claims benefit of Provisional Application No. 60/027,692, filed Oct. 10, 1996.

BACKGROUND OF THE INVENTION

This invention relates to the field of pharmaceutical and organic chemistry and provides benzo[b]thiophene compounds, intermediates, formulations, and methods.

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosomax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

Estrogen dependent cancers are major diseases affecting both women and to a lesser extent men. Cancer cells of this type are dependent on a source of estrogen to maintain the original tumor as well as to proliferate and metastasize to other locations. The most common forms of estrogen dependent cancer are breast and uterine carcinomas. Current chemotherapy of these diseases relies primarily on the use of anti-estrogens, predominately tamoxifen. The use of tamoxifen, although efficacious, is not without undesirable side-effects, e.g., estrogen agonist properties, such as uterine hypertrophy and carcinogenic potential. Compounds of the current invention while showing the same or better potential for anti-cancer activity also demonstrate a lower potential for estrogen agonist activity.

Thus, it would be a significant contribution to the art to provide novel compounds useful, for example, in the treatment or prevention of the disease states as indicated herein.

SUMMARY OF THE INVENTION

The present invention relates to compounds of formula I

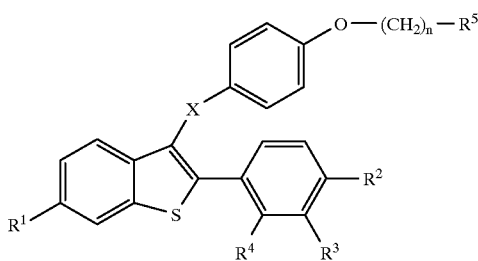

wherein $R^1$ is —COOR$^6$, —C≡CH, —CH=CH$_2$, or —COCH$_3$;

$R^2$ is —H, —Cl, —F, C$_1$-C$_4$ alkyl, —OH, —O(C$_1$-C$_4$ alkyl), —OCO(C$_1$-C$_6$ alkyl), —O—CO—O(C$_1$-C$_6$ alkyl), —O—CO—AR, —OSO$_2$(C$_2$-C$_6$ alkyl), or —O—CO—OAR, where AR is optionally substituted phenyl;

$R^3$ and $R^4$ are, independently, $R^2$;

$R^5$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino;

$R^6$ is —H or C$_1$-C$_4$ alkyl;

X is —CO— or —CH$_2$—; and n is 2 or 3;

or a pharmaceutically acceptable salt or solvate thereof.

The present invention further relates to pharmaceutical compositions containing compounds of formula I and methods for the therapeutic use of such compounds and compositions.

DETAILED DESCRIPTION OF THE INVENTION

The present invention further provides intermediate compounds of formula II which are novel and useful for preparing the pharmaceutically active compounds of the present invention, and are shown below.

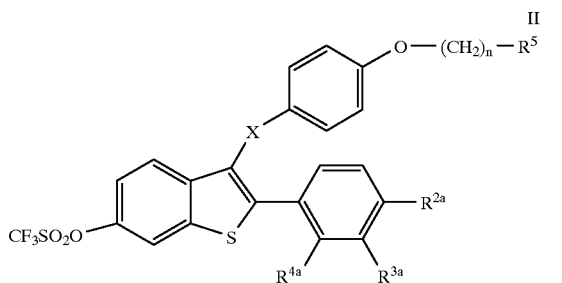

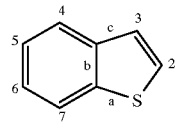

The starting material for preparing compounds of the present invention is a compound of formula III or IIIa.

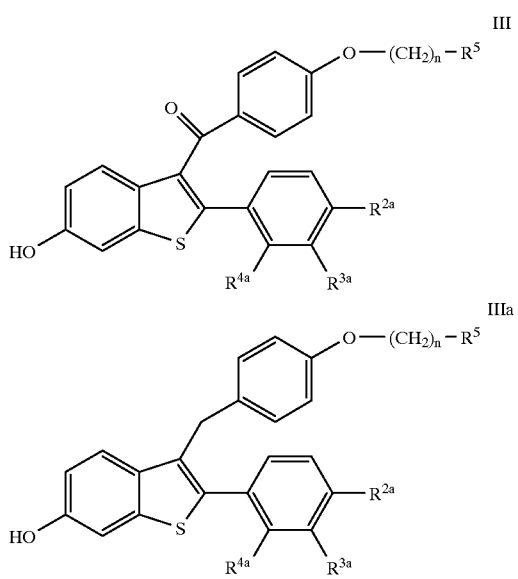

wherein
$R^{2a}$, $R^{3a}$, and $R^{4a}$ are, independently, —H, —Cl, —F, $C_1$—$C_4$ alkyl, or —$OR^7$, where $R^7$ is a hydroxyl protecting group; and
$R^5$, X and n have their previous meanings.

A preferred compound of formula II is [2-[4-(t-Butyldimethylsilyloxy)phenyl]-6-trifluoromethylsulfonoyloxy benzo[b]thien-3-yl][4-[2-(1-piperidinyl)ethoxy]phenyl]methanone.

General terms used in the description of compounds herein described bear their usual meanings. For example, "$C_1$–$C_6$ alkyl" refers to straight or branched aliphatic chains of 1 to 6 carbon atoms including moieties such as methyl, ethyl, propyl, isopropyl, butyl, n-butyl, pentyl, isopentyl, hexyl, isohexyl, and the like. Similarly, the term "—$OC_1$–$C_4$ alkyl" represents a $C_1$–$C_4$ alkyl group attached through an oxygen molecule and include moieties such as, for example, methoxy, ethoxy, n-propoxy, isopropoxy, and the like. Of these alkoxy groups, methoxy is highly preferred in most circumstances.

Optionally substituted phenyl includes phenyl and phenyl substituted once or twice with $C_1$–$C_6$ alkyl, $C_1$–$C_4$ alkoxy, hydroxy, nitro, chloro, fluoro, or tri (chloro or fluoro)methyl.

The term, "hydroxyl protecting group ($R^7$)" contemplates numerous functionalities used in the literature to protect a hydroxyl function during a chemical sequence and which can be removed to yield the phenol. Included within this group would be acyls, mesylates, tosylates, benzyl, alkylsilyloxys, —$OC_1$–$C_4$ alkyls, and the like. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and The Peptides, Vol. I, Schrooder and Lubke, Academic Press (London and New York, 1965). A preferred hydroxyl protecting group for the current invention is tert-butyl-dimethylsilyloxy (TBDMS), (see: examples and preparations, below).

The term "inhibit" includes its generally accepted meaning which includes prohibiting, preventing, restraining, alleviating, ameliorating, and slowing, stopping or reversing progression, severity, or a resultant symptom. As such, the present method includes both medical therapeutic and/or prophylactic administration, as appropriate.

The compounds of the current invention are named as derivatives of centrally located carbon, i.e., the "—CO—" or "—$CH_2$—" moiety in formula I, thus derivatives are methanones or methanes, e.g. a compound of A—CO—B, would be named [A][B]methanone. Further the compounds of formula I are derivatives of benzo[b]thiophene which is named and numbered according to the Ring Index, The American Chemical Society, as follows:

wherein $R^{2a}$, $R^{3a}$, $R^{4a}$, $R^5$, and n have their previous meanings.

Compounds of formula III are generally known in the art and are prepared essentially as described by Jones, et al., in U.S. Pat. Nos. 4,400,543 and 4,418,068 each of which is herein incorporated by reference. See also, Jones, et al., *J. Med. Chem.*, 27, p. 1057–1066 (1984). The compounds of formula IIIa are prepared as described by Bryant, et al., in U.S. Pat. Nos. 5,484,798 and 5,492,921, each of which is herein incorporated by reference. Compounds of formula III or IIIa, where $R^{2a-4a}$ are —$OR^7$ may be prepared by reacting their hydroxy precursors with the proper number of equivalents of protecting reagent which will allow the $C_6$ hydroxyl group to remain unprotected. This protection synthesis usually results in a statistical distribution of protecting groups on the various hydroxyl functions. These products can be separated by chromatographic techniques to yield the desired compound of III or IIIa, i.e., a compound with an unprotected 6-hydroxyl. An example of this preparation, using the preferred TBDMS protecting group, is given below.

The compounds of formula III or IIIa are converted into their triflate analogs, i.e., the compounds of formula II, by reaction of the phenol with a trifluoromethylsulfonoylating agent in the presence of an acid scavenger. Commonly used sulfonoylating reagents would be halides, e.g., trifluoromethylsulfonoyl-chloride, -bromide, or -iodide, anhydrides mixed or homogeneous, e.g., triflic anhydride, or imides, e.g., N-alkyl or aryl trifluoromethylsulfonylimide. A preferred reagent is N-phenyltrifluoromethanesulfonimide.

Acid scavengers used in the synthesis of the compounds of formula II include alkali metal bases, e.g., $Na_2CO_3$, $K_2CO_3$, etc. or organic tertiary amines, e.g., trimethylamine, pyridine, lutidine, triethylamine, etc. A preferred acid scavenger is triethylamine.

This reaction may be run in a variety of inert solvents, such as ether, THF, dioxane, methylene chloride, and the like. Of these, THF is preferred and especially preferred is the anhydrous form of THF.

The sulfonoylation reaction may be run at temperatures between 0–50° C., with ambient temperature adequate and most convenient. Under these reaction conditions, the reaction is usually complete within one to twenty hours. The optimal time can be determined by monitoring the progress of the reaction via conventional chromatographic techniques, such as tlc.

Application of the chemistry described, supra, enables the preparation of the compounds of formula II. Examples of the compounds of formula II include, but are not limited to:

[2-[4-(t-butyldimethylsilyloxy)phenyl]-6-trifluoromethylsulfonoyloxybenzo[b]thien-3-yl][4-[2-(1-piperidinyl)ethoxy]phenyl]methanone

[2-[4-(t-butyldimethylsilyloxy)phenyl]-6-trifluoromethylsulfonoyloxybenzo[b]thien-3-yl][4-[2-(1-piperidinyl)ethoxy]phenyl]methane

[2-[3-(t-butyldimethylsilyloxy)phenyl]-6-trifluoromethylsulfonoyloxybenzo[b]thien-3-yl][4-[2-(1-piperidinyl)ethoxy]phenyl]methanone

[2-[2-(t-butyldimethylsilyloxy)phenyl]-6-trifluoromethylsulfonoyloxybenzo[b]thien-3-yl][4-[2-(1-piperidinyl)ethoxy]phenyl]methanone

[2-[4-(t-butyldimethylsiiyioxy)phenyl]-6-trifluoromethylsulfonoyloxybenzo[b]thien-3-yl][4-[2-(1-pyrrolidinyl)ethoxy]phenyl]methanone

[2-[4-(t-butyldimethylsilyloxy)phenyl]-6-trifluoromethylsulfonoyloxybenzo[b]thien-3-yl][4-[3-(1-piperidinyl)propoxy]phenyl]methanone

[2-[3-chloro-4-(t-butyldimethylsilyloxy)phenyl]-6-trifluoromethylsulfonoyloxybenzo[b]thien-3-yl][4-[2-(1-piperidinyl)ethoxy]phenyl]methanone

[2-[3-(t-butyldimethylsilyloxy)-4-fluorophenyl]-6-trifluoromethylsulfonoyloxybenzo[b]thien-3-yl][4-[2-(1-piperidinyl)ethoxy]phenyl]methane

[2-[2-methyl-4-(t-butyldimethylsilyloxy)phenyl]-6-trifluoromethylsulfonoyloxybenzo[b]thien-3-yl][4-[2-(1-piperidinyl)ethoxy]phenyl]methanone

[2-[4-(t-butyldimethylsilyloxy)phenyl]-6-trifluoromethylsulfonoyloxybenzo[b]thien-3-yl][4-[2-(1-hexamethyleneimino)ethoxy]phenyl]methanone

[2-[4-(t-butyldimethylsilyloxy)phenyl]-6-trifluoromethylsulfonoyloxybenzo[b]thien-3-yl][4-[2-(N,N-dimethylamino)ethoxy]phenyl]methane

[2-[3-fluoro-4-(t-butyldimethylsilyloxy)phenyl]-6-trifluoromethylsulfonoyloxybenzo[b]thien-3-yl][4-[3-(1-piperidinyl)propoxy]phenyl]methanone

[2-[3,4-di-(t-butyldimethylsilyloxy)phenyl]-6-trifluoromethylsulfonoyloxybenzo[b]thien-3-yl][4-[2-(1-piperidinyl)ethoxy]phenyl]methanone

[2-[2,4-di-(t-butyldimethylsilyloxy)phenyl]-6-trifluoromethylsulfonoyloxybenzo[b]thien-3-yl][4-[2-(1-piperidinyl)ethoxy]phenyl]methane

[2-[2,3-di-(t-butyldimethylsilyloxy)phenyl]-6-trifluoromethylsulfonoyloxybenzo[b]thien-3-yl][4-[2-(1-pyrrolidinyl)ethoxy]phenyl]methanone

[2-[2,3-di-chlorophenyl]-6-trifluoromethylsulfonoyloxybenzo[b]thien-3-yl][4-[2-(1-pyrrolidinyl)ethoxy]phenyl]methanone

[2-[4-fluorophenyl]-6-trifluoromethylsulfonoyloxybenzo[b]thien-3-yl][4-[2-(1-pyrridinyl)ethoxy]phenyl]methanone

[2-[2-methyl-3-fluorophenyl]-6-trifluoromethylsulfonoyloxybenzo[b]thien-3-yl][4-[2-(1-pyrridinyl)ethoxy]phenyl]methanone

[2-[3-methyl-4-chlorophenyl]-6-trifluoromethylsulfonoyloxybenzo[b]thien-3-yl][4-[2-(1-piperidinyl)ethoxy]phenyl]methanone

[2-[3,4-di-methoxyphenyl]-6-trifluoromethylsulfonoyloxybenzo[b]thien-3-yl][4-[2-(1-pyrridinyl)ethoxy]phenyl]methanone

[2-[4-methoxyphenyl]-6-trifluoromethylsulfonoyloxybenzo[b]thien-3-yl][4-[2-(1-piperidinyl)ethoxy]phenyl]methanone

[2-[4-methoxyphenyl]-6-trifluoromethylsulfonoyloxybenzo[b]thien-3-yl][4-[2-(1-piperidinyl)ethoxy]phenyl]methane The triflate compounds of formula II are converted to certain compounds of formula Ia'–Ic' by a transition metal coupling reaction. Transition metals such as, but not limited to, palladium and nickel, in various oxidation states, are generally employed. Typically, these reactions are run in inert solvents which would include toluene, DMF, acetonitrile, and the like. Catalytic amounts of phosphorous-bearing ligands are used to facilitate these reactions, e.g., triarylphosphines, bis-diphenylphosphoalkanes, bis-diphenylphosphinoferrocenes and the like. A preferred phospho-ligand is bis-1,3-diphenylphosphinopropane. Organic bases are also employed to facilitate the reaction, e.g., trialkylamines, pyridine, etc. A preferred base is triethylamine. The temperature employed in this coupling is that which is sufficient to effect completion of the reaction, generally, in the range from 50–100° C. The length of time required for the reaction to run to completion is typically from four to seventy-two hours. However, the optimal time can be determined by monitoring the progress of the reaction via conventional chromatographic techniques.

When the preferred hydroxyl protecting group ($R^7$), i.e., TBDMS, is present in a compound of formula II, this protecting group is cleaved during the coupling reaction and subsequent workup. Thus, the products (Ia'–Ic') are isolated as the free hydroxyl derivatives. This chemistry is illustrated in Scheme I, below.

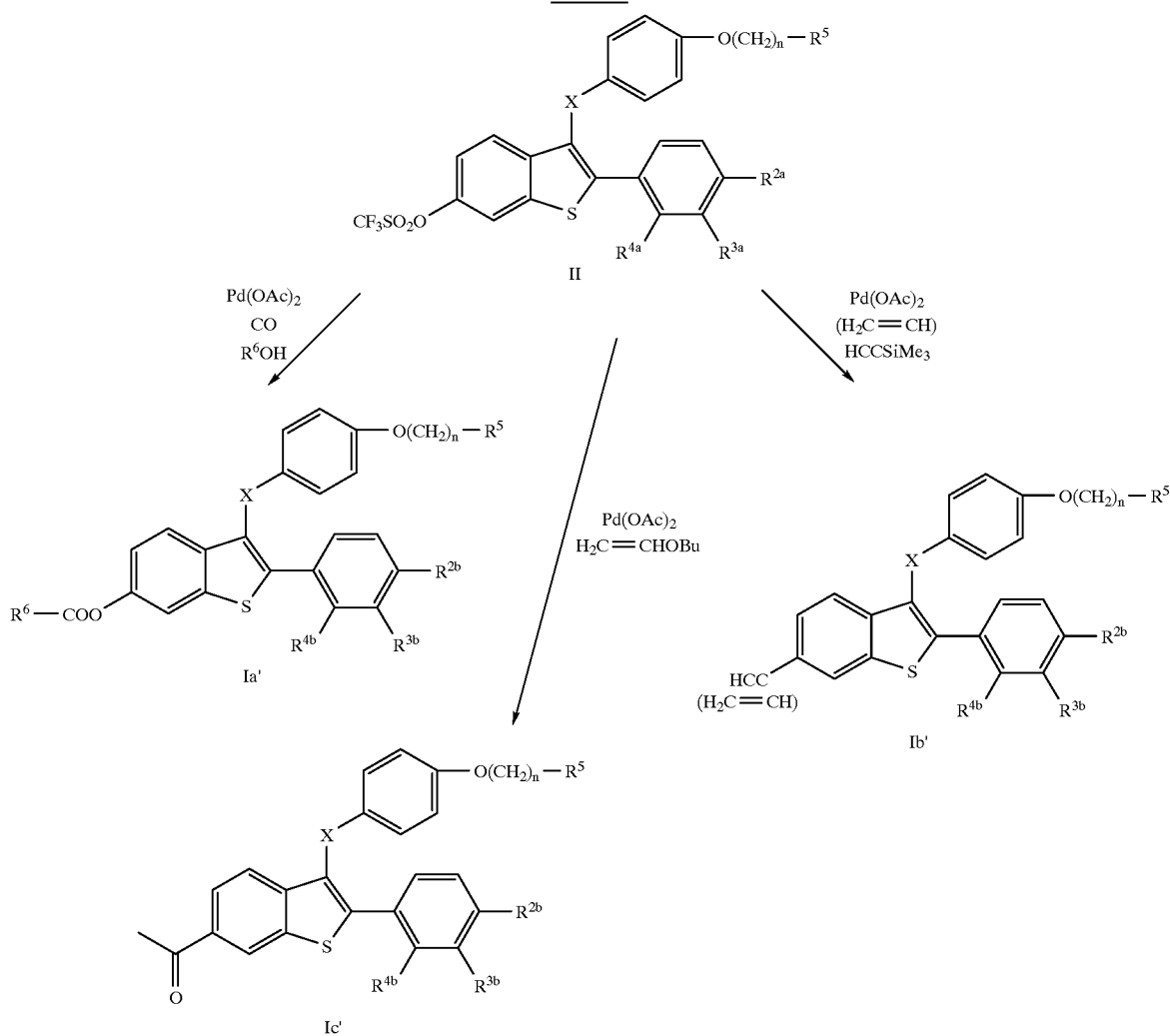

Scheme I wherein $R^{2b}$, $R^{3b}$, and $R^{4b}$ are, independently, —H, —Cl, —F, $C_1$–$C_4$ alkyl, or —OH; and $R^5$, $R^6$, n, and X have their previous meanings.

The compounds of formula Ia', where the triflate has been replaced by a carbonyl (acid or ester), are prepared by running the metal coupling reaction in the presence of carbon monoxide and using either water or an alcohol as a co-solvent/reactant. The use of water in this reaction leads to the formation of the 6-acid derivatives. The use of an alcohol ($R^6$OH) in this reaction leads to the formation of the ester derivatives. Specific examples of these reactions enabling the preparation of the compounds of formula Ia' are given below. Further information regarding this chemistry may be found in: Dolle, et al., Joural of the Chemical Society, Chemical Communications, 904–905 (1987). An alternate method of preparing the 6-carboxylic acid derivatives would be to hydrolyze one of the esters to the carboxylic acid. This hydrolysis can be done with either basic or acid catalysis. Basic catalysis is preferred; especially preferred is the use of LiOH.

Application of the chemical synthesis described, supra, enables the preparation of the compounds of formula Ia'. Compounds of formula Ia' include, but are not limited to:

[2-(4-hydroxyphenyl)-6-methoxycarbonylbenzo[b]thien-3-yl][4-[2-(1-piperidinyl)ethoxy]phenyl]methanone

[2-(4-hydroxyphenyl)-6-methoxycarbonylbenzo[b]thien-3-yl][4-[2-(1-piperidinyl)ethoxy]phenyl]methane

[2-(4-hydroxyphenyl)-6-ethoxycarbonylbenzo[b]thien-3-yl][4-[2-(1-piperidinyl)ethoxy]phenyl]methanone

[2-(4-hydroxyphenyl)-6-n-butyloxycarbonylbenzo[b]thien-3-yl][4-[2-(1-piperidinyl)ethoxy]phenyl]methanone

[2-(4-hydroxyphenyl)-6-1-propyloxycarbonylbenzo[b]thien-3-yl][4-[2-(1-piperidinyl)ethoxy]phenyl]methanone

[2-(4-fluorophenyl)-6-methoxycarbonylbenzo[b]thien-3-yl][4-[2-(1-piperidinyl)ethoxy]phenyl]methanone

[2-(4-methoxyphenyl)-6-methoxycarbonylbenzo[b]thien-3-yl][4-[2-(1-piperidinyl)ethoxy]phenyl]methanone

[2-(3-hydroxyphenyl)-6-methoxycarbonylbenzo[b]thien-3-yl][4-[2-(1-pyrridinyl)ethoxy]phenyl]methanone

[2-(2-methyl-4-hydroxyphenyl)-6-methoxycarbonylbenzo[b]thien-3-yl][4-[3-(1-piperidinyl)propoxy]phenyl]methane

[2-(3,4-di-methoxyphenyl)-6-ethyloxycarbonylbenzo[b]thien-3-yl][4-[2-(1-piperidinyl)ethoxy]phenyl]methanone

[2-(4-hydroxyphenyl)-6-methyloxycarbonylbenzo[b]thien-3-yl][4-[2-(1-piperidinyl)ethoxy]phenyl]methanone

[2-(4-hydroxyphenyl)-6-methyloxycarbonylbenzo[b]thien-3-yl][4-[2-(1-piperidinyl)ethoxy]phenyl]methane

[2-(4-methoxyphenyl)-6-methyloxycarbonylbenzo[b]thien-3-yl][4-[2-(1-piperidinyl)ethoxy]phenyl]methanone

[2-(4-fluorophenyl)-6-carbonylbenzo[b]thien-3-yl][4-[2-(1-piperidinyl)ethoxy]phenyl]methanone

[2-(2-fluorophenyl)-6-methoxycarbonylbenzo[b]thien-3-yl][4-[2-(1-piperidinyl)ethoxy]phenyl]methanone

[2-(2,3-di-fluorophenyl)-6-methoxycarbonylbenzo[b]thien-3-yl][4-[2-(1-piperidinyl)ethoxy]phenyl]methane

[2-(3-methylphenyl)-6-methoxycarbonylbenzo[b]thien-3-yl][4-[2-(N,N-dimethylamino)ethoxy]phenyl]methanone

[2-(2-ethylphenyl)-6-methoxycarbonylbenzo[b]thien-3-yl][4-[3-(1-piperidinyl)propoxy]phenyl]methanone and the like.

The compounds of formula Ib', where the triflate has been replaced by acetylene or vinyl, are prepared by running the coupling reaction in the presence of trimethylsilylacetylene or trimethylsilylethylene. Such chemistry is illustrated in the examples below. Further information regarding this chemistry may be found in: Chen, et al., Tetrahedron Letters, 27(10), p. 1171–1174 (1986).

Application of the chemical synthesis described, supra, enables the preparation of the compounds of formula Ib', which include, but are not be limited to:

[2-(4-hydroxyphenyl)-6-ethynylbenzo[b]thien-3-yl][4-[2-(1-piperidinyl)ethoxy]phenyl]methanone

[2-(4-hydroxyphenyl)-6-ethynylbenzo[b]thien-3-yl][4-[2-(1-piperidinyl)ethoxy]phenyl]methane

[2-(4-hydroxyphenyl)-6-ethenylbenzo[b]thien-3-yl][4-[2-(1-piperidinyl)ethoxy]phenyl]methanone

[2-(4-hydroxyphenyl)-6-ethenylbenzo[b]thien-3-yl][4-[2-(1-piperidinyl)ethoxy]phenyl]methane

[2-(4-fluorophenyl)-6-ethynylbenzo[b]thien-3-yl][4-[2-(1-piperidinyl)ethoxy]phenyl]methanone

[2-(4-methoxyphenyl)-6-ethynylbenzo[b]thien-3-yl][4-[2-(1-piperidinyl)ethoxy]phenyl]methanone

[2-(4-methoxyphenyl)-6-ethenylbenzo[b]thien-3-yl][4-[2-(1-piperidinyl)ethoxy]phenyl]methanone

[2-(3-hydroxyphenyl)-6-ethynylbenzo[b]thien-3-yl][4-[2-(1-pyrridinyl)ethoxy]phenyl]methanone

[2-(2-methyl-4-hydroxyphenyl)-6-ethynylbenzo[b]thien-3-yl][4-[3-(1-piperidinyl)propoxy]phenyl]methane

[2-(3,4-di-methoxyphenyl)-6-ethynylbenzo[b]thien-3-yl][4-[2-(1-piperidinyl)ethoxy]phenyl]methanone

[2-(3,4-di-methoxyphenyl)-6-ethenylbenzo[b]thien-3-yl][4-[2-(1-piperidinyl)ethoxy]phenyl]methanone

[2-(4-hydroxyphenyl)-6-ethynylbenzo[b]thien-3-yl][4-[3-(1-piperidinyl)propoxy]phenyl]methanone

[2-(4-hydroxyphenyl)-6-ethynylbenzo[b]thien-3-yl][4-[3-(1-piperidinyl)propoxy]phenyl]methane

[2-(4-methoxyphenyl)-6-ethenylbenzo[b]thien-3-yl][4-[2-(1-pyrrolidinyl)ethoxy]phenyl]methanone

[2-(4-hydroxyphenyl)-6-ethynylbenzo[b]thien-3-yl][4-[2-(1-hexamethyleneimino)ethoxy]phenyl]methanone

[2-(4-hydroxyphenyl)-6-ethynylcarbonylbenzo[b]thien-3-yl][4-[2-(1-morpholino)ethoxy]phenyl]methanone

[2-(4-hydroxyphenyl)-6-ethynylcarbonylbenzo[b]thien-3-yl][4-[2-(N,N-di-ethylamino)ethoxy]phenyl]methanone The compounds of formula Ic', where the triflate has been replaced by the 6-methylketo function, are prepared by running the coupling reaction in the presence of butylvinylether. The chemistry enabling the preparation of the compounds of formula Ic' is given below. Further information regarding this chemistry may be found in: Cabri,et al., J. Med. Chem., 55, p. 3654–3655 (1990).

Application of the chemical synthesis described, supra, enables the preparation of the compounds of formula Ic', which include, but are not limited to:

[2-(4-hydroxyphenyl)-6-acetylbenzo[b]thien-3-yl][4-[2-(1-piperidinyl)ethoxy]phenyl]methanone

[2-(4-hydroxyphenyl)-6-acetylbenzo[b]thien-3-yl][4-[2-(1-piperidinyl)ethoxy]phenyl]methane

[2-(4-hydroxyphenyl)-6-acetylbenzo[b]thien-3-yl][4-[2-(1-pyrrolidinyl)ethoxy]phenyl]methanone

[2-(4-hydroxyphenyl)-6-acetylbenzo[b]thien-3-yl][4-[2-(1-pyrrolidinyl)ethoxy]phenyl]methane

[2-(4-fluorophenyl)-6-acetylbenzo[b]thien-3-yl][4-[2-(1-piperidinyl)ethoxy]phenyl]methanone

[2-(4-methoxyphenyl)-6-acetylbenzo[b]thien-3-yl][4-[2-(1-piperidinyl)ethoxy]phenyl]methanone

[2-(4-methoxyphenyl)-6-acetylbenzo[b]thien-3-yl][4-[3-(1-piperidinyl)propoxy]phenyl]methanone

[2-(3-hydroxyphenyl)-6-acetylbenzo[b]thien-3-yl][4-[2-(1-pyrridinyl)ethoxy]phenyl]methanone

[2-(2-methyl-4-hydroxyphenyl)-6-acetylbenzo[b]thien-3-yl][4-[3-(1-piperidinyl)propoxy]phenyl]methane

[2-(3,4-di-methoxyphenyl)-6-acetylbenzo[b]thien-3-yl][4-[2-(1-piperidinyl)ethoxy]phenyl]methanone

[2-(3,4-di-methoxyphenyl)-6-acetylbenzo[b]thien-3-yl][4-[2-(1-piperidinyl)ethoxy]phenyl]methane

[2-(2-chloro-4-hydroxyphenyl)-6-acetylbenzo[b]thien-3-yl][4-[3-(1-piperidinyl)propoxy]phenyl]methanone

[2-(3-ethyl-4-hydroxyphenyl)-6-acetylbenzo[b]thien-3-yl][4-[3-(1-piperidinyl)propoxy]phenyl]methane

[2-(4-methoxyphenyl)-6-acetylbenzo[b]thien-3-yl][4-[2-(1-hexamethyleneimino)ethoxy]phenyl]methanone

[2-(3-fluoro-4-hydroxyphenyl)-6-acetylbenzo[b]thien-3-yl][4-[2-(1-hexamethyleneimino)ethoxy]phenyl]methanone

[2-(4-hydroxyphenyl)-6-acetylcarbonylbenzo[b]thien-3-yl][4-[2-(1-morpholino)ethoxy]phenyl]methanone

[2-(4-hydroxyphenyl)-6-acetylcarbonylbenzo[b]thien-3-yl][4-[2-(N,N-di-ethylamino)ethoxy]phenyl]methanone Other compounds of formula I are prepared by replacing the 2', 3', and/or 4'-position hydroxy moieties, when present, with a moiety of the formula —O—CO—($C_1$-$C_6$ alkyl), —O—CO—Ar, or —O—$SO_2$—($C_2$-$C_6$ alkyl) via well known procedures. See, e.g., U.S. Pat. Nos. 5,393,763 or 5,482,949, each of which is incorporated herein by reference.

For example, when an —O—CO($C_1$-$C_6$ alkyl) or —O—CO-phenyl group is desired, a mono-, di-, trihydroxy compound of formula Ia', Ib', or Ic' is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger, such as a tertiary amine, has been added. If desired, acylation catalysts such as 4-dimethylaminopyridine or 4-pyrrolidinopyridine may be used. See, e.g., Haslam, et al., *Tetrahedron*, 36:2409–2433 (1980).

The present reactions are carried out at moderate temperatures, in the range from about −25° C. to about 100°

C., frequently under an inert atmosphere such as nitrogen gas. However, ambient temperature is usually adequate for the reaction to run.

Acylation of a 2', 3', and/or 4'-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

When a formula I compound is desired in which the 2', 3', and/or 4'-position hydroxy group of a formula Ia', Ib', or Ic' compound is converted to a group of the formula —O—SO$_2$—(C$_2$–C$_6$ alkyl), the mono-, di-, or trihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The hydroxy compounds also can be reacted with the appropriate sulfonic anhydride or mixed sulfonic anhydrides. Such reactions are carried out under conditions such as were explained above in the discussion of reaction with acid halides and the like.

Applying the chemical synthetic schemes, supra, compounds of formula I may be prepared, and such compounds would include, but not be limited to:

[2-(4-acetyloxyphenyl)-6-methoxycarbonylbenzo[b]thien-3-yl][4-[2-(1-piperidinyl)ethoxy]phenyl]methanone

[2-(4-hexanoyloxyphenyl)-6-methoxycarbonylbenzo[b]thien-3-yl][4-[2-(1-piperidinyl)ethoxy]phenyl]methanone

[2-(4-benzoyloxyphenyl)-6-methoxycarbonylbenzo[b]thien-3-yl][4-[2-(1-piperidinyl)ethoxy]phenyl]methanone

[2-(4-n-butylsulfonoyloxyphenyl)-6-methoxycarbonylbenzo[b]thien-3-yl][4-[2-(1-piperidinyl)ethoxy]phenyl]methanone

[2-(4-benzoyloxyphenyl)-6-methoxycarbonylbenzo[b]thien-3-yl][4-[2-(1-piperidinyl)ethoxy]phenyl]methane

[2-(4-acetyloxyphenyl)-6-methoxycarbonylbenzo[b]thien-3-yl][4-[2-(1-piperidinyl)ethoxy]phenyl]methane

[2-(4-benzoyloxyphenyl)-6-ethoxycarbonylbenzo[b]thien-3-yl][4-[2-(1-piperidinyl)ethoxy]phenyl]methanone

[2-(4-propanoyloxyphenyl)-6-n-butyloxycarbonylbenzo[b]thien-3-yl][4-[2-(1-piperidinyl)ethoxy]phenyl]methanone

[2-(4-n-butylsulfonoyloxyphenyl)-6-1-propyloxycarbonylbenzo[b]thien-3-yl][4-[2-(1-piperidinyl)ethoxy]phenyl]methanone

[2-(3-acetyloxy-4-fluorophenyl)-6-methoxycarbonylbenzo[b]thien-3-yl][4-[2-(1-piperidinyl)ethoxy]phenyl]methanone

[2-(2-benzoyloxy-4-methoxyphenyl)-6-methoxycarbonylbenzo[b]thien-3-yl][4-[2-(1-piperidinyl)ethoxy]phenyl]methanone

[2-(3-hydroxy-4-acetyloxyphenyl)-6-methoxycarbonylbenzo[b]thien-3-yl][4-[2-(1-pyrridinyl)ethoxy]phenyl]methanone

[2-(2-methyl-4-hexanoyloxyphenyl)-6-methoxycarbonylbenzo[b]thien-3-yl][4-[3-(1-piperidinyl)propoxy]phenyl]methane

[2-(4-butanoyloxyphenyl)-6-ethynylbenzo[b]thien-3-yl][4-[2-(1-piperidinyl)ethoxy]phenyl]methanone

[2-(4-benzoyloxyphenyl)-6-ethynylbenzo[b]thien-3-yl][4-[2-(1-piperidinyl)ethoxy]phenyl]methanone

[2-(4-n-butylsulfonoyloxyphenyl)-6-ethynylbenzo[b]thien-3-yl][4-[2-(1-piperidinyl)ethoxy]phenyl]methanone

[2-(4-acetyloxyphenyl)-6-ethynylbenzo[b]thien-3-yl][4-[2-(1-piperidinyl)ethoxy]phenyl]methane

[2-(4-benzoyloxyphenyl)-6-ethenylbenzo[b]thien-3-yl][4-[2-(1-piperidinyl)ethoxy]phenyl]methanone

[2-(4-butanoyloxyphenyl)-6-ethenylbenzo[b]thien-3-yl][4-[2-(1-piperidinyl)ethoxy]phenyl]methane

[2-(3-acetyloxy-4-fluorophenyl)-6-ethynylbenzo[b]thien-3-yl][4-[2-(1-piperidinyl)ethoxy]phenyl]methanone

[2-(2-benzoyloxy-4-methoxyphenyl)-6-ethynylbenzo[b]thien-3-yl][4-[2-(1-piperidinyl)ethoxy]phenyl]methanone

[2-(3-chloro-4-acetyloxyphenyl)-6-ethenylbenzo[b]thien-3-yl][4-[2-(1-piperidinyl)ethoxy]phenyl]methanone

[2-(3-hydroxy-4-n-butylsulfonoyloxyphenyl)-6-ethynylbenzo[b]thien-3-yl][4-[2-(1-pyrridinyl)ethoxy]phenyl]methanone

[2-(2-methyl-4-hexanoyloxyphenyl)-6-ethynylbenzo[b]thien-3-yl][4-[3-(1-piperidinyl)propoxy]phenyl]methane

[2-(3,4-di-acetyloxyphenyl)-6-ethynylbenzo[b]thien-3-yl][4-[2-(1-piperidinyl)ethoxy]phenyl]methanone

[2-(3,4-di-benzoyloxyphenyl)-6-ethenylbenzo[b]thien-3-yl][4-[2-(1-piperidinyl)ethoxy]phenyl]methanone

[2-(4-acetyloxyphenyl)-6-acetylbenzo[b]thien-3-yl][4-[2-(1-piperidinyl)ethoxy]phenyl]methanone

[2-(4-butanoyloxyphenyl)-6-acetylbenzo[b]thien-3-yl][4-[2-(1-piperidinyl)ethoxy]phenyl]methanone

[2-(4-benzoyloxyphenyl)-6-acetylbenzo[b]thien-3-yl][4-[2-(1-piperidinyl)ethoxy]phenyl]methanone

[2-(4-n-butylsulfonoyloxyphenyl)-6-acetylbenzo[b]thien-3-yl][4-[2-(1-piperidinyl)ethoxy]phenyl]methanone

[2-(4-acetyloxyphenyl)-6-acetylbenzo[b]thien-3-yl][4-[2-(1-piperidinyl)ethoxy]phenyl]methane

[2-(4-benzoyloxyphenyl)-6-acetylbenzo[b]thien-3-yl][4-[2-(1-pyrrolidinyl)ethoxy]phenyl]methanone

[2-(4-hexanoyloxyphenyl)-6-acetylbenzo[b]thien-3-yl][4-[2-(1-pyrrolidinyl)ethoxy]phenyl]methane

[2-(3-acetyloxy-4-fluorophenyl)-6-acetylbenzo[b]thien-3-yl][4-[2-(1-piperidinyl)ethoxy]phenyl]methanone

[2-(2-fluoro-4-benzoyloxyphenyl)-6-acetylbenzo[b]thien-3-yl][4-[2-(1-piperidinyl)ethoxy]phenyl]methanone

[2-(3-fluoro-4-butanoyloxyphenyl)-6-acetylbenzo[b]thien-3-yl][4-[3-(1-piperidinyl)propoxy]phenyl]methanone

[2-(3-acetyloxyphenyl)-6-acetylbenzo[b]thien-3-yl][4-[2-(1-pyrridinyl)ethoxy]phenyl]methanone

[2-(2-methyl-4-propanoyloxyphenyl)-6-acetylbenzo[b]thien-3-yl][4-[3-(1-piperidinyl)propoxy]phenyl]methane

[2-(3,4-di-benzoyloxyphenyl)-6-acetylbenzo[b]thien-3-yl][4-[2-(1-piperidinyl)ethoxy]phenyl]methanone

[2-(3,4-di-benzoyloxyphenyl)-6-acetylbenzo[b]thien-3-yl][4-[2-(1-piperidinyl)ethoxy]phenyl]methane

[2-(2-chloro-4-pentanoyloxyphenyl)-6-acetylbenzo[b]thien-3-yl][4-[3-(1-piperidinyl)propoxy]phenyl]methanone

[2-(3-ethyl-4-acetyloxyphenyl)-6-acetylbenzo[b]thien-3-yl][4-[3-(1-piperidinyl)propoxy]phenyl]methane Preferred embodiments of the current invention are [2-(4-hydroxyphenyl)-6-methoxycarbonylbenzo[b]thien-3-yl][4-[2-(1-piperidinyl)ethoxy]phenyl]methanone hydrochloride and [2-(4-hydroxyphenyl)-6-ethynylbenzo[b]thien-3-yl][4-[2-(1-piperidinyl)ethoxy]phenyl]methanone.

Together, the compounds of formulae Ia', Ib', Ic', and their corresponding acyl and sulfonoyl derivatives comprise the genus of the compounds of formula I, are novel, and useful for the pharmacologic methods herein described.

Although the free-base form of formula I compounds can be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. Preferred salts are the hydrochloride and oxalate salts.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

The term "solvate" represents an aggregate that comprises one or more molecules of the solute, such as a formula I compound, with one or more molecules of solvent.

The following examples are presented to further illustrate the preparation of compounds of the present invention. It is not intended that the invention be limited in scope by reason of any of the following examples.

NMR data for the following Examples were generated on a GE 300 MHz NMR instrument, and anhydrous d-6 DMSO was used as the solvent unless otherwise indicated.

Preparation 1

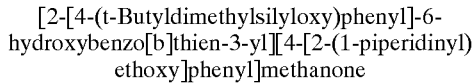

[2-[4-(t-Butyldimethylsilyloxy)phenyl]-6-hydroxybenzo[b]thien-3-yl][4-[2-(1-piperidinyl)ethoxy]phenyl]methanone A solution was prepared consisting of 10 g (21.1 mmol) of [2-(4-hydroxyphenyl)-6-hydroxybenzo[b]thien-3-yl][4-[2-(1-piperidinyl)ethoxy]phenyl]methanone and 6 g (49.1 mmol) of dimethylaminopyridine in 700 mL of THF-DMF (6:1)(v/v). This solution was stirred for one hour at ambient temperature and then cooled to 0° C. in an ice bath. To this solution was added 2.9 g (19.3 mmol) of tert-butyl-dimethylsilylchloride. The reaction mixture was stirred under a nitrogen atmosphere and allowed to warm to ambient temperature. After seventy-two hours, the reaction was quenched with the addition of a saturated solution of aqueous NH$_4$Cl. The organic layer was separated and washed with water, brine, and finally dried by filtration through anhydrous Na$_2$SO$_4$ and evaporated to dryness The crude product was triturated with CH$_2$Cl$_2$, allowed to stand for three hours, and filtered to remove unreacted starting material. This resulting product is a mixture of isomers, which are separated by chromatography on a silica gel column eluted with a linear gradient beginning with CHCl$_3$ and ending with CHCl$_3$—MeOH (19:1)(v/v). The desired fractions were determined by tlc, combined, and evaporated to dryness. This yielded 5.1 g of the title compound, isolated as a yellow crystalline solid.

PMR: δ 0.12(s,6H); 0.92(s,9H); 1.46(m,2H); 1.67(m,4H); 2.56(m,5H); 2.79(t, J=5.6 Hz, 2H); 4.07(t, J=5.7 Hz, 2H); 6.55(d, J=8.9 Hz, 2H); 6.66(d, J=8.5 Hz, 2H); 6.77(dd, J$_1$=8.7 Hz, J$_2$=2.2 Hz, 1H); 7.17(d, J=2.2 Hz, 1H); 7.20(d, J=8.6 Hz, 3H); 7.44(d, J=8.8 Hz, 1H); 7.63(d, J=8.9 Hz, 2H); MS: m/e=587 (M) FD; EA: Calc. for C$_{34}$H$_{41}$NO$_4$SSi: C, 69.47; H, 7.03; N, 2.38 Found: C, 69.19; H, 6.98; N, 2.57.

Preparation 2

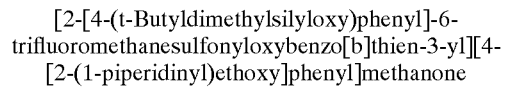

[2-[4-(t-Butyldimethylsilyloxy)phenyl]-6-trifluoromethanesulfonyloxybenzo[b]thien-3-yl][4-[2-(1-piperidinyl)ethoxy]phenyl]methanone A solution was prepared of 10 g (17.5 mmol) of [2-[4-(t-butyldimethylsilyloxy)phenyl]-6-hydroxybenzo[b]thien-3-yl][4-[2-(1-piperidinyl)ethoxy]phenyl]methanone in 100 mL of CH$_2$Cl$_2$, which was placed under a nitrogen atmosphere and cooled to 0° C. in an ice bath. Triethylamine (5 mL, 3.6 g, 35.9 mmol) was added followed by the addition of 7 g (19.5 mmol) of N-phenyltrifluoromethanesulfonimide. The reaction was allowed to warm slowly to ambient temperature over a period of sixteen hours. The reaction mixture was filtered and evaporated to a red oil. The crude product was chromatographed on a silica gel column eluted with CH$_2$Cl$_2$. This yielded 11 g of the title compound isolated as a tan amorphous solid.

PMR: (CDCl$_3$) δ 0.05 (s, 6H); 0.85(s, 9H); 1.35(m, 2H); 1.55(m, 4H); 2.40(m,4H); 2.65(t, J=7 Hz, 2H); 4.00(t, J=7 Hz, 2H); 6.65(m, 4H); 7.20(m, 3H); 7.65(d, J=10 Hz, 2H); 7.75(m,2H); MS: m/e=720 (M) FD

EXAMPLE 1

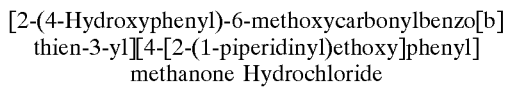

[2-(4-Hydroxyphenyl)-6-methoxycarbonylbenzo[b]thien-3-yl][4-[2-(1-piperidinyl)ethoxy]phenyl] methanone Hydrochloride A reaction mixture was prepared consisting of 1 g (1.4 mmol) of [2-[4-(t-butyldimethylsilyloxy)phenyl]-6-trifluoromethanesulfonyloxybenzo[b]thien-3-yl][4-[2-(1-piperidinyl)ethoxy]phenyl] methanone, 5 mL of triethylamine, 5 mL of MeOH, and 60 mg (0.14 mmol) of bis-diphenylphosphinopropane in 15 mL of anhydrous DMF. The reaction was stirred at ambient temperature and purged with electronic-grade carbon monoxide, and 30 mg (0.14 mmol) of Pd(II) (AcO)$_2$ was added. The reaction solution changed color from light orange to dark brown. The reaction mixture was heated to 75° C. under a carbon monoxide atmosphere for six hours. The reaction was allowed to cool to ambient temperature and the solvents were removed by evaporation in vacuo. The residue was suspended in THF and filtered to remove the catalyst and other insolubles. The THF was removed by evaporation. The residue was dissolved in 100 mL of EtOAc and 100 mL of 1N HCl was added. The reaction was vigorously stirred at ambient temperature for two hours. The pH of the aqueous layer was adjusted to 4–5 with HOAc—NaOAc buffer, and the aqueous layer was separated and extracted three times with 100 mL portions of EtOAc. All the EtOAc extracts were combined and dried with $Na_2SO_4$ and evaporated to dryness. The crude product was further purified by chromatography on a silica gel column eluted with a linear gradient beginning with $CH_2Cl_2$ and ending with $CH_2Cl_2$—MeOH (85:15)(v/v). The free base of the product was converted to its hydrochloride salt by dissolving the residue in 50 mL of THF and adding THF saturated with HCl. The product is obtaining by evaporating the volatiles. This yielded 540 mg of the title compound isolated as a white powder, mp: 128° C. (dec.).

PMR: δ 1.35–1.90 (m, 6H); 2.90–3.10 (m, 4H); 3.45 (m,2H); 3.95 (s, 3H); 4.35 (s br, 2H); 6.80 (d, J=8 Hz, 2H); 7.05 (d J=8 Hz, 2H); 7.35 (d, J=8 Hz, 2H); 7.65 (d, J=8 Hz, 1H); 7.80(d J=8 Hz, 2H); 8.00 (d, J=8 Hz, 1H); 8.80 (s, 1H); 10.00 (s, 1H); MS: m/e=515 (M-HCl) FD; EA: Calc. for $C_{30}H_{29}NO_5S$-HCl-1.5$H_2O$: C, 62.24; H, 5.75; N, 2.42 Found: C, 61.90; H, 5.60; N, 2.19.

EXAMPLE 2

[2-(4-Hydroxyphenyl)-6-n-butoxycarbonylbenzo[b] thien-3-yl][4-[2-(1-piperidinyl)ethoxy]phenyl] methanone In a manner similar to that used in Example 1, only using n-butanol as a reactant, 410 mg of the title compound was prepared as its free base and isolated as a white powder, mp: 87–90° C.

PMR: ($CDCl_3$) δ 1.05 (t, J=6 Hz, 3H); 1.65 (qnt, J=6 Hz, 2H); 1.80 (s br, 2H); 1.90 (sxt, J=6 Hz, 2H); 2.05 (d br, 2H); 2.15–2.30 (m, 2H); 2.90–3.05 (m, 2H); 3.50 (s br, 2H); 3.75 (d br, 2H); 4.45–4.55 (m, 4H); 6.70 (d, J=10 Hz, 2H); 6.75 (d, J=10 Hz, 2H); 7.15 (d, J=8 Hz, 2H); 7.65 (d, J=10 Hz, 2H); 8.25 (q, $J_1$=12 Hz, $J_2$=8 Hz, 2H); 8.70 (s, 1H); MS: m/e=558 (M-HCl) FD; EA: Calc. for $C_{33}H_{35}NO_5S$-2$H_2O$: C, 66.76; H, 6.62; N, 2.36; S, 5.40 Found: C, 66.37; H, 6.04; N, 2.24; S, 5.60.

EXAMPLE 3

[2-(4-Hydroxyphenyl)-6-(3-methyl) proxycarbonylbenzo[b]thien-3-yl][4-[2-(1-piperidinyl)ethoxy]phenyl]methanone In a manner similar to that used in Example 1, only using sec-butanol as a reactant, 430 mg of the title compound was prepared as its free base and isolated as a white powder, mp: 95–98° C.

PMR: ($CDCl_3$) δ 1.15 (d, J=6 Hz, 6H); 1.75 (s br, 2H); 1.85–1.95 (m, 1H); 2.10 (s br, 3H); 2.15 (sxt, J=5 Hz, 1H); 3.10–3.30 (m, 4H); 3.40 (s br, 2H); 4.25 (d, J=7 Hz, 2H); 4.45 (s br, 2H); 6.70 (d, J=10 Hz, 2H); 6.80 (d, J=10 Hz, 2H); 7.20 (d, J=8 Hz, 2H); 7.65 (d, J=8 Hz, 2H); 8.15 (q, $J_1$=2 Hz, $J_2$=8 Hz, 2H); 8.70 (s, 1H); MS: m/e=558 (M-HCl) FD; EA: Calc. for $C_{33}H_{35}NO_5S$-2$H_2O$: C, 66.76; H, 6.62; N, 2.36; S, 5.40 Found: C, 66.57; H, 6.06; N, 2.32; S, 5.52.

EXAMPLE 4

[2-(4-Hydroxyphenyl)-6-carboxybenzo[b]thien-3-yl] [4-[2-(1-piperidinyl)ethoxy]phenyl]methanone Hydrochloride A solution was prepared by dissolving 2 g (4.0 mmol) of [2-(4-hydroxyphenyl)-6-methoxycarbonylbenzo[b]thien-3-yl][4-[2-(1-piperidinyl)ethoxy]phenyl]methanone and 0.2 g (8.0 mmol) of LiOH in 100 mL of THF and 10 mL of water. The reaction mixture was heated to reflux for eighteen hours. The reaction was allowed to cool and the solvents were removed by evaporation. The residue was partioned between 300 mL of EtOAc and 300 mL of 1N HCl. The product precipitated out and was removed by filtration and dried. This yielded 700 mg of the title compound as a yellow powder.

PMR: δ 1.3–1.5 (m,2H); 1.5–1.6 (m, 4H); 2.4–2.6 (m,4H); 2.7–2.8 (m, 2H); 4.1–4.2 (m,2H); 6.75 (d, J=8 Hz, 2H); 6.95 (d, J=8 Hz, 2H); 7.30 (d, J=8 Hz, 2H); 7.55 (d, J=8 Hz, 1H); 7.75 (d, J=8 Hz, 2H); 7.95 (d, J=8 Hz, 1H); 8.65 (s, 1H); MS: m/e=501 (M$^+$-Cl) FD; EA: Calc. for $C_{29}H_{27}NO_5S$-HCl-1.5$H_2O$: C, 61.66; H. 5.53; N, 2.48 Found: 61.91; H, 5.47; N, 2.31.

EXAMPLE 5

[2-(4-Hydroxyphenyl)-6-acetylbenzo[b]thien-3-yl] [4-[2-(1-piperidinyl)ethoxy]phenyl]methanone A solution was prepared consisting of 1 g (1.4 mmol) of [2-[4-(t-butyldimethylsilyloxy)phenyl]-6-trifluoromethamesulfonoylxybenzo[b]thien-3-yl][4-[2-(1-piperidinyl)ethoxy]phenyl]methanone, 1.1 mL (7.7 mmol) of butylvinylether, 1 mL of triethylamine, 60 mg (0.14 mmol) of bis-diphenylphosphinopropane, and 30 mg (0.14 mmol) of Pd(II)(AcO)$_2$ in 15 mL of anhydrous DMF. The reaction mixture was heated to 75° C., under a nitrogen atmosphere for five hours. The reaction mixture was allowed to cool and 15 mL of 5 N HCL was added. The reaction mixture was stirred for sixteen hours at ambient temperature. The reaction mixture was evaporated to dryness, suspended in THF, and filtered. The product was further purified by chromatography as described in Example 1, supra. This yielded 430 mg of the title compound as an orange solid, mp: 97–100° C.

PMR: δ 1.40 (s br, 2H); 1.80 (s br, 4H); 2.70 (s, 3H); 3.35 (s br, 4H); 3.45 (s br, 2H); 4.40 (s br, 2H); 6.75 (d, J=8 Hz, 2H); 7.00 (d, J=8 Hz, 2H); 7.30 (d, J=8 Hz, 2H); 7.55 (d, J=8 Hz, 1H); 7.75 (d, J=8 Hz, 2H); 7.90 (d, J=8 Hz, 1H); 8.80 (s, 1H); 10.00 (s, 1H); MS: m/e=499 (M$^+$) FD; EA: Calc. for $C_{30}H_{29}NO_4S$-$H_2O$: C, 69.61; H, 6.04; N, 2.71; S, 6.19 Found: 69.44; H, 6.20; N, 3.09; S, 5.84.

EXAMPLE 6

[2-(4-Hydroxyphenyl)-6-ethynylbenzo[b]thien-3-yl] [4-[2-(1-piperidinyl)ethoxy]phenyl]methanone A solution was prepared consisting of 2 g (2.8 mmol) of [2-[4-(t-butyldimethylsilyloxy)phenyl]-6-trifluoromethamesulfonyloxybenzo[b]thien-3-yl][4-[2-(1-piperidinyl)ethoxy]phenyl]methanone, 1.0 mL (0.68 g, 6.9 mmol) of trimethylsilylacetylene, 5 mL of triethylamine, 120 mg (0.28 mmol) of bis-diphenylphosphinopropane, and 60 mg (0.28 mmol) of Pd(II)(AcO)$_2$ in 20 mL of anhydrous DMF. The reaction mixture was heated to 75° C. for ten hours, under a nitrogen atmosphere. The reaction was allowed to cool and evaporated to dryness. The residue was suspended in 100 mL of THF and filtered and evaporated dryness. The residue was dissolved in 100 mL of EtOAc and 100 mL of 1N HCl. The reaction mixture was stirred vigorously for two hours. The organic layer was separated and evaporated to dryness. The residue was dissolved in 100 mL of THF and 0.5 g (2.7 mmol) of $Et_4NF-2H_2O$ was added and the reaction mixture was stirred for sixteen hours at ambient temperature, under a nitrogen atmosphere. The reaction mixture was evaporated to dryness and purified by chromatography of a silica gel column eluted with a linear gradient beginning with $CHCl_3$ and ending with $CHCl_3$—MeOH (4:1)(v/v). This yielded 300 mg of the title compound isolated as a tan solid, mp: 97–100° C.

PMR: ($CDCl_3$) δ 1.60 (s br, 2H); 1.80 (s br,4H); 2.80 (s br, 4H); 3.00 (t, J=3 Hz, 2H); 3.25 (s, 1H); 4.25 (t, J=3 Hz, 2H); 6.75–6.80 (m,4H); 7.25 (d, J=8 Hz, 2H); 7.60 (d, J=10 Hz, 1H); 7.75 (d, J=10 Hz, 2H); 7.85 (d, J=10 Hz, 1H); 8.10 (s, 1H); MS: m/e=481 ($M^+$) FD; EA: Calc. for $C_{30}H_{27}NO_3S$-$H_2O$: C, 72.12; H, 5.85; N, 2.80 Found: C, 72.27; H, 6.11; N, 2.66.

TEST PROCEDURE

General Preparation Procedure

In the examples illustrating the methods, a post-menopausal model was used in which effects of different treatments upon circulating lipids were determined.

Seventy-five day old female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room is 12 hours light and 12 hours dark.

Dosing Regimen Tissue Collection. After a one week acclimation period (therefore, two weeks post-OVX) daily dosing with test compound is initiated. 17α-ethynyl estradiol or the test compound are given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine: Xylazine (2:1, V:V) mixture and a blood sample is collected by cardiac puncture. The animals are then sacrificed by asphyxiation with $CO_2$, the uterus is removed through a midline incision, and a wet uterine weight is determined.

Cholesterol Analysis. Blood samples are allowed to clot at ambient temperature for 2 hours, and serum is obtained following centrifugation for 10 minutes at 3000 rpm. Serum cholesterol is determined using a Boehringer Mannheim Diagnostics high performance cholesterol assay. Briefly, the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve.

Uterine Eosinophil Peroxidase (EPO) Assay. Uteri are kept at 4° C. until time of enzymatic analysis. The uteri are then homogenized in 50 volumes of 50 mM Tris buffer (pH—8.0) containing 0.005% Triton X-100. Upon addition of 0.01% hydrogen peroxide and 10 mM o-phenylenediamine (final concentrations) in Tris buffer, increase in absorbance is monitored for one minute at 450 nm. The presence of eosonophils in the uterus is an indication of estrogenic activity of a compound. The maximal velocity of a 15 second interval is determined over the initial, linear portion of the reaction curve.

Source of Compound: 17α-ethynyl estradiol was obtained from Sigma Chemical Co., St. Louis, Mo.

The pharmacologic activity for the methods of the current invention, i.e., the compounds of formula I, are illustrate in Table 1, below.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitized x-rays generated and analyzed by an image analysis program (NIH image) at the distal metaphysis. The proximal aspect of the tibiae from these animals are also scanned by quantitative computed tomography.

In accordance with the above procedures, compounds of the present invention and ethynyl estradiol ($EE_2$) in 20% hydroxypropyl β-cyclodextrin are orally administered to test animals.

TABLE 1

| Compound | Dose mg/kg[a] | Uterine Wt. (% Inc.)[b] | Uterine EPO (Vmax)[c] | Serum Cholesterol (% Dec.)[d] |
|---|---|---|---|---|
| $EE_2$[e] | 0. | 171.2* | 142.4* | 85.1* |
| Example 1 | 0.1 | 46.9* | 4.5 | −8.6 |
| | 1 | 19.1 | 4.8 | 42.5* |
| | 10 | 45.2* | 7.5 | 56.1* |
| Example 2 | 0.1 | 19.4 | 2.4 | −1.2 |
| | 1.0 | 16.8 | 0.0 | 26.7 |
| | 10.0 | 52.5* | 4.8 | 55.6* |
| Example 3 | 0.1 | 11.8 | 3.3 | −2.4 |
| | 1.0 | 21.7 | 3.3 | 8.7 |
| | 10.0 | 47.1* | 4.8 | 58.0* |
| Example 4 | 0.1 | 18.8 | 3.3 | 0.6 |
| | 1.0 | 27.2 | 3.0 | 10.4 |
| | 10.0 | 29.6* | 3.6 | 44.9* |
| Example 5 | 0.1 | 18.8 | 1.2 | −6.3 |
| | 1.0 | 51.8* | 2.1 | 20.4 |
| | 10.0 | 69.4* | 5.4 | 45.4* |
| Example 6 | 0.1 | 14.3 | 3.9 | 39.4* |
| | 1.0 | 27.8 | 4.8 | 58.7* |
| | 10.0 | 22.5 | 4.8 | 65.8* |

*$p < 0.05$
[a]mg/kg PO
[b]Uterine Weight, % increase versus the ovariectomized controls
[c]Eosinophil peroxidase, $V_{maximum}$
[d]Serum cholesterol decrease versus ovariectomized controls
[e]17-α-Ethynyl-estradiol As evidence of the current invention treat estrogen dependent cancer, the following assay was performed.

MCF-7 Proliferation Assay

MCF-7 breast adenocarcinoma cells (ATCC HTB 22) were maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid] 10 mM}, nonessential amino acids and bovine insulin (1 ug/mL) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium [Ca++/Mg++ free HBSS (phenol red-free) supplemented with 10 mM HEPES and 2 mM EDTA]. Cells were washed twice with assay medium and adjusted to 80,000 cells/mL. Approximately 100 mL (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 mL transferred to triplicate microcultures followed by 50 mL assay medium for a final volume of 200 mL. After an additional 48 hours at 37° C. in a 5% $CO_2$ humidified incubator, microcultures were pulsed with tritiated thymidine (1 $\mu$Ci/well) for 4 hours. Cultures were terminated by freezing at −70° C. for 24 hours followed by thawing and harvesting of microcultures using a Skatron Semiautomatic Cell Harvester. Samples were counted by liquid scintillation using a Wallac BetaPlace β counter. The compounds of formula I are active and potent in inhibiting the tumor cell growth, see: Table 2.

TABLE 2

| Compound | $IC_{50}$ (nM) |
| --- | --- |
| Example 1 | 40 |
| Example 2 | 45 |
| Example 3 | 45 |
| Example 5 | 60 |
| Example 6 | 20 |

As used herein, the term "effective amount" means an amount of compound of the present invention which is capable of inhibiting the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, alone or in combination with another pharmaceutical agent, generally will be administered in a convenient formulation. A typical dosage amount is from about 5 mg to about 600 mg, 1 to 3 times a day. More typically, the dose will be about 15 mg to 80 mg/day. The term of administration will be for a period of at least 2 months. More typically, administration will be at least 6 months, or chronically. The following formulation examples only are illustrative and are not intended to limit the scope of the present invention.

Formulations

In the formulations which follow, "active ingredient" means a compound of formula I, or a salt or solvate thereof.
Formulation 1: Gelatin Capsules
Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:
Formulation 2: Tablets

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3: Tablets

| Ingredient | Quantity (mg/tablet) |
| --- | --- |
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 4: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient | 50 mg |
| Isotonic saline | 1,000 mL |

The solution of the above ingredients is intravenously administered to a patient at a rate of about 1 mL per minute.

Formulation 8: Combination Capsule I

| Ingredient | Quantity (mg/capsule) |
| --- | --- |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 9: Combination Capsule II

| Ingredient | Quantity (mg/capsule) |
| --- | --- |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Formulation 10: Combination Tablet

| Ingredient | Quantity (mg/capsule) |
| --- | --- |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

We claim:
1. A compound of formula I

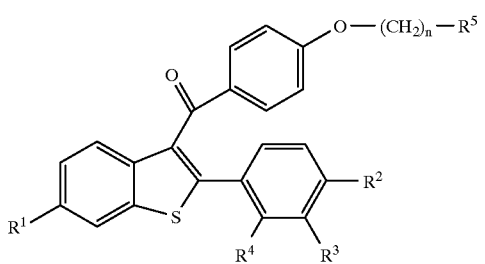

wherein
- $R^1$ is —COOR$^6$, —C≡CH, —CH=CH$_2$, or —COCH$_3$;
- $R^2$ is —H, —Cl, —F, $C_1$-$C_4$ alkyl, —OH, —O($C_1$-$C_4$ alkyl), —OCO($C_1$-$C_6$ alkyl), —O—CO—O($C_1$-$C_6$ alkyl), —O—CO—AR, —OSO$_2$($C_2$-$C_6$ alkyl), or —O—CO—OAR, where AR is optionally substituted phenyl;
- $R^3$ and $R^4$ are, independently, $R^2$;
- $R^5$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino;
- $R^6$ is —H or $C_1$-$C_4$ alkyl;
- X is —CO— or —CH$_2$—; and
- n is 2 or 3; with the proviso that when $R^2$ is —OH, —O($C_1$-$C_4$ alkyl), —OCO($C_1$-$C_6$ alkyl), —O—CO—O($C_1$-$C_6$ alkyl), or —O—CO—AR, then $R^1$ is not —COCH$_3$;

or a pharmaceutically acceptable salt or solvate thereof.

2. A compound according to claim 1 wherein X is —CO—.

3. A compound according to claim 2 wherein $R^2$ is methoxy.

4. A compound according to claim 2 wherein $R^2$ is hydroxy.

5. A compound according to claim 1 wherein $R^6$ is methyl.

6. A compound according to claim 1 wherein $R^1$ is —C≡CH.

7. A compound according to claim 1 wherein $R^1$ is acetyl.

8. A compound according to claim 1 wherein said compound is [2-(4-hydroxyphenyl)-6-methoxycarbonylbenzo[b]thien-3-yl][4-[2-(1-piperidinyl)ethoxy]phenyl]methanone hydrochloride.

9. A compound according to claim 1 wherein said compound is [2-(4-hydroxyphenyl)-6-ethynylbenzo[b]thien-3-yl][4-[2-(1-piperidinyl)ethoxy]phenyl]methanone.

10. A method of inhibiting bone loss in a human comprising the administration of a compound of formula I of claim 1 to a human in need thereof.

11. A method according to claim 10, wherein said human is a post-menopausal female.

12. A method of inhibiting a cardiovascular disease comprising the administration of a compound of formula I of claim 1 to a human in need thereof.

13. A method according to claim 12 wherein the cardiovascular disease is hyperlipidemia.

14. A method according to claim 12 wherein the human being treated is a post-menopausal female.

15. A method of inhibiting an estrogen-dependent cancer, comprising the administration of a compound of formula I of claim 1 to a human in need thereof.

16. A method according to claim 15 wherein the estrogen-dependent cancer is breast cancer.

17. A method according to claim 15 wherein the said human is a female.

18. A method according to claim 15 wherein the estrogen-dependent cancer is uterine cancer.

19. A pharmaceutical formulation comprising a compound of formula I of claim 1, and one or more pharmaceutically acceptable excipients, carriers, or diluents.

20. A compound of formula II

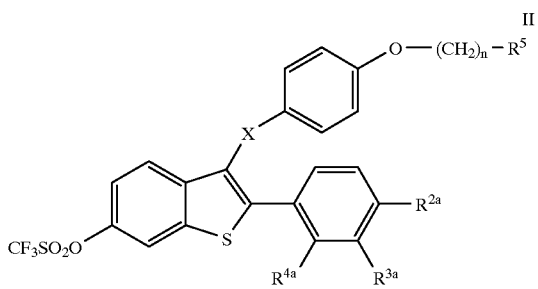

wherein
- $R^{2a}$, $R^{3a}$, and $R^{4a}$ are, independently, —H, —Cl, —F, $C_1$-$C_4$ alkyl, or —OR$^7$, where $R^7$ is a hydroxyl protecting group; and
- $R^5$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino;
- X is —CO— or —CH$_2$—; and
- n is 2 or 3;

or a pharmaceutically acceptable salt or solvate thereof.

21. A compound according to claim 20 wherein X is —CO—.

22. A compound according to claim 21 wherein $R^7$ is tert-butyldimethylsilyloxy.

23. A compound according to claim 20 wherein n is two.

24. A compound according to claim 23 wherein $R^5$ is piperidinyl.

25. A compound according to claim 20 wherein said compound is [2-[4-(t-butyldimethylsilyloxy)phenyl]-6-trifluoromethylsulfonoyloxybenzo[b]thien-3-yl][4-[2-(1-piperidinyl)ethoxy]phenyl]methanone.

* * * * *